United States Patent [19]

Pries et al.

[11] Patent Number: 5,694,930
[45] Date of Patent: Dec. 9, 1997

[54] DEVICE FOR QUALITATIVE AND/OR QUANTATIVE ANALYSIS OF A SAMPLE

[75] Inventors: Ralf H. Pries, Dortmund; Dae-Jin Yoon, Schwerte, both of Germany

[73] Assignee: Yoon-Ok Kim, Dortmund, Germany

[21] Appl. No.: 387,782

[22] PCT Filed: Aug. 19, 1993

[86] PCT No.: PCT/DE93/00757

§ 371 Date: May 15, 1995

§ 102(e) Date: May 15, 1995

[87] PCT Pub. No.: WO94/04909

PCT Pub. Date: Mar. 3, 1994

[30] Foreign Application Priority Data

Aug. 21, 1992 [DE] Germany .......................... 42 27 813.9

[51] Int. Cl.⁶ .............................. A61B 5/00; G01N 21/41
[52] U.S. Cl. .............................. 128/633; 356/136
[58] Field of Search .................. 128/633; 356/39, 356/135, 136, 137

[56] References Cited

U.S. PATENT DOCUMENTS 4,169,676 10/1979 Kaiser ........................ 356/39
4,422,714 12/1983 Benoit et al. .................. 356/136
4,692,024 9/1987 Bloss ........................... 356/135
4,704,029 11/1987 Van Heuvelen .................. 128/633

FOREIGN PATENT DOCUMENTS 40 00 583  7/1991  Germany .
92/06366  4/1992  WIPO .

Primary Examiner—Jennifer Bahr
Assistant Examiner—Eric F. Winakur
Attorney, Agent, or Firm—Antonelli, Terry, Stout & Kraus, LLP

[57] ABSTRACT

Disclosed is a device for qualitative and quantitative in-vitro or in-vivo analysis of a sample by means of ATC (Attenuated Total Reflectance) while utilizing at least one radiation source, an ATR element as well as a detector unit. The present invention is distinguished by the combination of the following features: the radiation source generating a primary beam aimed at the ATR element, the primary beam impinging on the ATR element at an angle of $\alpha$, which is larger than the critical angle of the total reflectance $\alpha_T$ at the interface between an optically dense medium and a less dense one; the to-be-analyzed sample whose layer near the surface interacts with the primary radiation can be disposed on at least one side of the ATR element, a detector unit corresponding to the incidence angle of said primary radiation in the ATR element detects the radiation emitted from the ATR element.

19 Claims, No Drawings

DEVICE FOR QUALITATIVE AND/OR QUANTATIVE ANALYSIS OF A SAMPLE

TECHNICAL FIELD

The present invention relates to a device for a qualitative and quantitative in-vitro or in-vivo analysis of a sample by means of attenuated total reflectance utilizing at least one radiation source, an ATR element as well as a detector unit.

STATE OF THE ART

Known is an analysis process for strongly absorbant materials, so-called "attenuated total reflectance" (ATR), first described in 1961 by Harrick and Fahrenfort. This is a reflection method that utilizes the physical phenomena at the interface of two media of different optical density.

If a beam of light impinges obliquely into a medium having a high refraction index $n_2$ onto an interface to an optically less dense medium having $n_1$, the beam is reflected back if the angle of incidence $\alpha$ (the angle between the incident beam of light and the perpendicular on the interface) exceeds the critical angle of total reflectance. A part of the electromagnetic energy, however, nonetheless penetrates to a depth of a few light wavelengths into the optically less dense medium (surface waves).

If the energy of this part returns completely into the medium having a higher refraction index, this is referred to as total reflectance. If, however, the electro-magnetic radiation penetrating into the optically less dense medium is absorbed, the corresponding wavelengths, respectively portions of energy are missing in the reflected ray.

ATR technology is based on this principle. It requires a special optical device which usually is placed in the sample area of a spectrometer. The ATR additional element is composed of a system of mirrors which directs the incident beam into a crystal usually in the form of a trapezoidally cut prism of high reflection factor (e.g. KRS5, Ge, AgCl, or the like), which is in contact with the to-be-examined surface of the sample. In Fahrenfort's original arrangement, total reflectance occurs once at the interface between the crystal and the sample. Presently flat crystal plates to which the sample is pressed from both sides are usually employed. The radiation enters through the bevelled narrow end of the crystal, is reflected back and forth between the surfaces (up to 50 times) and leaves the same through the other narrow crystal end. This type of ATR is also referred to as "multiple reflectance unit", the method as FMIR (frustrated multiple internal reflection) or just MIR.

The previously mentioned physical principles yield the conditions and possibilities of ATR technology. The following points are criteria for the realization of an ATR spectrum:

the difference between the refraction indices of the reflection element and of the sample at a selected wavelength.

the angle of incidence $\alpha$, the absorption of the sample, the optical contact between the ATR crystal and the sample, the number n of reflections within the crystal, the illuminated surface of the crystal, the depth of penetration of the surface wave into the sample.

Quantative measurements with ATR technology have hitherto not generally been possible, because the contact between the sample and the reflection element is dependent on the pressing force, respectively on the state of the surface of the sample.

DESCRIPTION OF THE INVENTION

The object of the present invention, therefore, is to provide a device for the analysis of the composition of a sample with which both high precision qualitative and quantitative analysis can be carried out not only in vitro but also in vivo. Primarily analysis/measurement precision should be improved compared to the known devices as well as detection ability, which is an important criterium for assessment of the quality of an analysis process. Furthermore, the object of the present invention is to develop a measuring head in miniaturized form which is orders of magnitudes smaller than conventional ATR additional elements.

An invented miniaturized measuring head opens totally new application possibilities extending far beyond those of the present state of the art.

The present invention is based, i.a. on the surprising revelation that this goal can be achieved by, e.g., using an ATR element of a most simple geometric shape, noteably, semi-cylindrical or hemispherical. Therefore, contrary to the state of the art, no complicatedly shaped crystals, which are usually not only expensive but also very sensitive sometimes even poisonous (KRS5!), are not required, but rather, e.g., simple, conventional plano-convex glass or plastic microlenses of hemispherical shape are employed.

Contrary to the state of the art ATR technology, single or multimode laser diodes (Fabry-Perot-type) having different wavelengths depending on the goal of the analysis are employed as the primary source of radiation. The invented apparatus requires, i.a., no monochromator. Single mode laser diodes themselves transmit, by way of illustration, strictly monochromatic radiation.

Depending on the emitted wavelength ranges of the laser diode(s) utilized as the primary radiation source(s), simple (usually not cooled) photodiodes (e.g., Ge detectors) are employed. The invented apparatus obviates the use of expensive arrays of diodes or photomultipliers.

Therefore, in accordance with the present invention a device is created which, on the one hand, holds the ATR element, and on the other hand also serves as a mount for one or several laser diodes and, furthermore, affords photodiodes (depending on the number of utilized laser diodes) support. The plane area of the ATR elements lies in a plane (hereinafter referred to as "base") with said holding device and later serves to receive the sample substance, respectively, can, e.g., be pressed against the sample substance to be examined. The curved interface of the ATR element extends into said holding device and simultaneously closes a cavity that serves as a light trap and can be designed in various manners.

The laser diode is disposed within said device in such a manner that it aims at an angle that is larger than the critical angle of the total reflection for the respective medium at the center point of the ATR element (respectively in the case of semi-cyclindrical ATR elements the center line). A photodiode corresponding to the laser diode is attached at the same angle, however, on the laser diode of the opposite side of the apparatus. To be noted is that the incident radiation angle (on the laser diode side) and radiation angle (on the detector side) must be identical.

The same, naturally, is the case if several laser diodes are used: the holding device permits the use of (practically) any number of laser diodes and the corresponding number of photodiodes. Depending on the shape of the utilized ATR elements, they can be arranged parallel to, respectively in a circle around the ATR element. As can be readily seen, according to this principle many different constellations can be realized, e.g. several laser diodes having the same wavelength but having a different angle of radiation, or several laser diodes having different wavelengths but having the same angle of radiation, or combinations of both possibilities.

The wavelengths of the radiation emitted by the laser diodes is very temperature and current dependent. Usually, therefore, an attempt is made, in addition to respective stabilization of current and power, to keep the temperature as constant as possible. In accordance with the state of the art, this is usually realized by cooling the laser diodes with fans, Peltier elements, fluid nitrogen, or the like.

As one self-calibrating method, the primary beam of the radiation source is used for generating a self-calibrating measurement signal using a current applied to the radiation source and a current generated by a photodiode of the radiation source for the self-calibration of a temperature of the radiation source. More particularly, information about an optical output power of the laser chip (i.e., given by a current generated by the photodiode) and information about a current applied to the radiation source can be obtained during an operation of the laser diode, and such information is useable to self-calibrate a temperature of the radiation source, i.e. as a laser chip alters its optical output power depending on its temperature, any shift in current generated by the photodiode is an indication of a shift in temperature. The radiation source can be site-dependent doped laser chip which has an inner structure thereof alterable by changing a current strength applied thereto such that varying electron density can be achieved which results in site-dependency of a refraction index so that emission of several pencils of rays of a same and/or varying wavelength occurs. More particularly, change of a current varies an electron density inside of the semiconductor, which in turn causes a change in the refraction index associated with the device. For relevant known art, attention is directed to the Melles Griot Catalog, copyright 1990, p. 20–58 through p. 20–61.

The present invention is, furthermore, based on understanding that suited temperature control of the laser diodes is also possible with thermistors. This is in particular the case by utilizing barristers (PTC resistors) which are employed as heating elements to raise the temperature of the laser diode to a value above the ambient temperature not attainable solely with the laser current. On the basis of their special characteristic line, the employed PTC resistors are simultaneously utilized as control elements. A (if need be also several) PTC resistor is brought into contact with the housing of the laser diode, preferably with the flange.

Described is a device (measuring head, sensor head) for qualitative and/or quantative in-vitro or in-vivo analysis of the composition of a sample.

The invented device has the combination of the following features:
  at least one laser diode is provided which emits radiation at a specific angle in
  a geometrically as simple as possible designed ATR element on the plane base of which the sample substance to be examined can be positioned
  as well as at least one radiation detector corresponding to the laser diode,
  furthermore the apparatus contains at least one PTC resistor in order to control the laser diode.

The invented apparatus is distinguished by its simplicity which permits a very small size. This yields a wide range of possible applications of which only the use in analyzing human tissue, in particular in in-vivo examination of body fluids as well as particularly in non-invasive analysis of components of human blood (blood glucose, cholesterol, alcohol, etc.) are mentioned.

A compensation arrangement can be constructed to utilize changes in physical parameters such as temperatures, power, current strength as well as other physical parameters depending on a pressure with which a sample is applied to the ATR element, for analysis of the example. Further, the compensation arrangement can utilize physical changes in air such as temperature for analysis of the sample. More particularly, such parameters (measured by appropriate sensors) can be utilized for compensating for an influence of such parameters on the measurements, therefore to enable a better analysis of the sample.

What is claimed is:

1. A device for qualitative and quantitative in-vitro or in-vivo analysis of a sample by means of attenuated total reflectance, said device comprising:
  at least one radiation source, an ATR (Attenuated Total Reflectance) element and at least one detector unit, said radiation source generating a primary beam aimed at the ATR element, said primary beam impinging on said ATR element at an angle of $\alpha$, which angle is larger than a critical angle of a total reflectance $\alpha_T$ at an interface between an optically dense medium and a less dense one, a to-be-analyzed sample being disposed on at least one side of said ATR element, so that the primary beam interacts with a surface-layer of said sample, with said detector unit being arranged to detect emergent radiation from said ATR element, wherein said ATR element, said at least one radiation source being combined with a PTC resistor, and said at least one detector unit are integrated in one single mounting component, said ATR element being hemispherical, semi-cylindrical or irregular in shape and the to-be-analyzed sample being in contact with a plane surface of said ATR element while the primary beam is aimed through the convex side and reflected at the plane side of said ATR element.

2. A device according to claim 1, wherein said primary beam is used for generating a self-calibrating measurement signal by using a current applied to said radiation source and a current generated by a photodiode of said radiation source, for self-calibration of a temperature of said radiation source.

3. A device according to claim 1, wherein said radiation source is a laser diode whose wavelength stability is ensured by constant temperature control means which is directly attached to said radiation source.

4. A device according to claim 3, wherein said temperature control means is said PTC resistor (barrister) having a constant temperature can be set above an ambient temperature thereof.

5. A device according to claim 3, wherein said temperature control means is a Peltier element a set to a predetermined temperature.

6. A device according to claim 3, wherein said laser diode is multi-mode operable.

7. A device according to claim 3, wherein an energy supply of said irradiation source as well as said constant temperature control means are self-calibrating.

8. A device according to claim 3, wherein said radiation source is more particularly a site-dependent doped laser chip having an inner structure thereof being alterable by changing a current strength applied thereto such that varying electron density can be achieved which results in site-dependency of a refraction index so that emission of several radiation pencils of rays of a same and/or varying wavelengths occur.

9. A device according to claim 1, wherein said ATR element is a plano convex glass or plastic lens.

10. A device according to claim 1, wherein by said detector unit is an uncooled photodiode.

11. A device according to claim 1, wherein said ATR element is positioned in said mounting component in such a manner that it can be inserted with its convex side inside a recess in said mounting component and thereby contracting an interior cavity serving as a light trap.

12. A device according to claim 11, wherein a further detector is mounted inside said recess, said component serving to measure the reflectance radiation.

13. A device according to claim 1, wherein said light source and said detector unit is arranged according to the angle of incidence and of reflection.

14. A device according to claim 1, further comprising compensation means for utilizing changes in physical parameters such as temperature, power, current strength as well as other physical parameters depending on a pressure with which said sample being applied onto said ATR element, for analysis of a sample substance.

15. A device according to claim 1, further comprising compensation means for utilizing physical changes in air such as temperature, for analysis of a sample substance.

16. A device according to claims 14 or 15, wherein said compensation means provides compensation of changes of physical parameters caused by the sample and air using mathematical evaluation algorithms including multi-linear regression arrangements.

17. A device according to claim 1, further comprising means to irradiate more than one radiation bundle of rays from said radiation source into said ATR element, so as to effect an analysis based upon varying interactions with said sample at different depths of penetration.

18. A device according to claim 1, further comprising an air referencing arrangement wherein a reference measurement of the detected radiation is measured in air prior to and/or following every sample analysis.

19. A device according to claim 18, wherein said device is more specifically for non-invasive analysis of blood components such as blood glucose, cholesterol, alcohol, wherein said device further comprises an arrangement to accommodate a skin section through which blood is circulating, preferably in the region of a finger print, on a measuring surface of said ATR element in such a manner that a measuring success is substantially independent of a pressure with which the skin section is placed thereon.

* * * * *